United States Patent [19]

Kraft et al.

[11] 4,281,536
[45] Aug. 4, 1981

[54] APPARATUS FOR TESTING THE CONTAMINATION OF INDUSTRIAL LIQUIDS

[75] Inventors: Thomas L. Kraft; Howard A. Vick; James W. Meador, all of Houston, Tex.

[73] Assignee: KVM Engineering, Inc., Houston, Tex.

[21] Appl. No.: 74,595

[22] Filed: Sep. 12, 1979

[51] Int. Cl.³ .............................................. G01N 7/14
[52] U.S. Cl. .......................................... 73/53; 73/19; 73/52
[58] Field of Search ............... 73/53, 52, 61.3, 64.2, 73/19

[56] References Cited

U.S. PATENT DOCUMENTS

| 2,603,086 | 7/1952 | Ingham, Jr. et al. | 73/19 |
| 2,648,977 | 8/1953 | Mills | 73/52 |
| 2,749,744 | 6/1956 | Doudera, Jr. et al. | 73/52 |

FOREIGN PATENT DOCUMENTS

| 1278762 | 2/1963 | Fed. Rep. of Germany | 73/19 |
| 2519895 | 11/1976 | Fed. Rep. of Germany | 73/61.3 |
| 652257 | 4/1951 | United Kingdom | 73/52 |

Primary Examiner—Gerald Goldberg
Assistant Examiner—Joseph W. Roskos
Attorney, Agent, or Firm—Michael P. Breston

[57] ABSTRACT

The test apparatus detects pressure changes in a vessel containing a volume of a contaminated industrial liquid and a volume of gas. The apparatus includes a detector having a housing defining a chamber. A pressure transducer having a flexible, pressure-transmitting wall is mounted in the chamber. A passageway fluidly communicates between a port in the housing and the transducer. In one embodiment a needle housing is removably coupled to the port. A hollow needle is adapted to pierce a stopper in the vessel. The vessel remains continuously sealed during and after the pressure test. Pressure changes in the gas of the vessel are transmitted through the needle and the passageway to the transducer. The transducer converts such pressure changes into corresponding electric signals which are indicative of the density of organisms in the liquid contained in the vessel. In another embodiment, the gas in the vessel is coupled to a pressure-responsive, threshold switch for detecting when the gas in the vessel reaches a threshold pressure.

3 Claims, 5 Drawing Figures

U.S. Patent  Aug. 4, 1981  Sheet 1 of 2  4,281,536
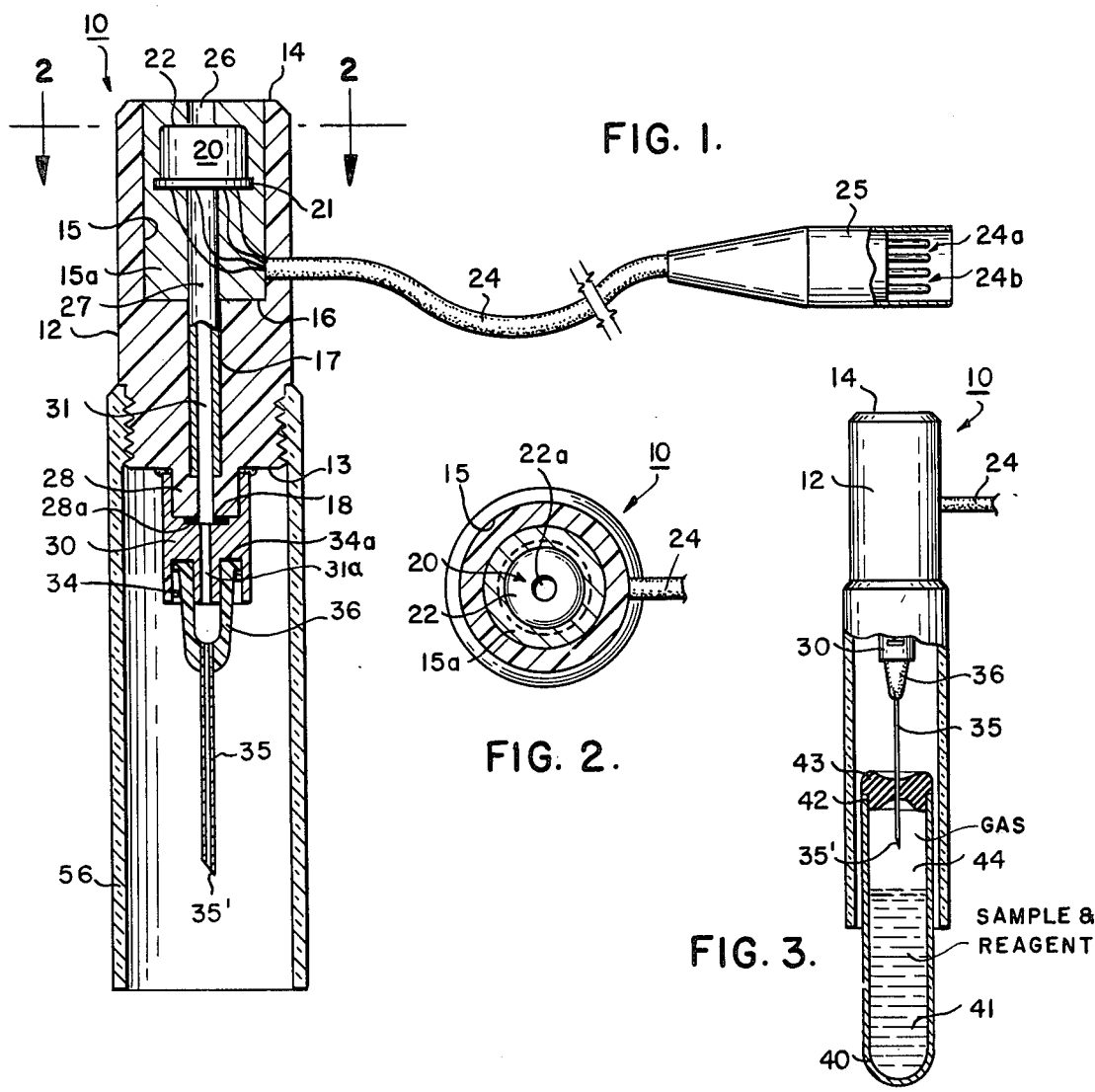
FIG. 1.
FIG. 2.
FIG. 3.
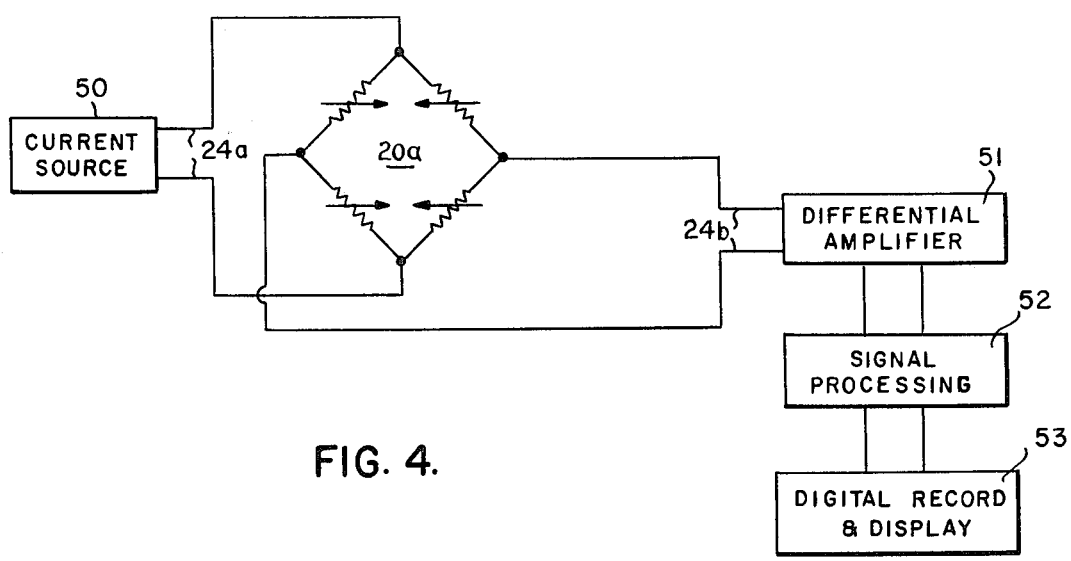
FIG. 4.

APPARATUS FOR TESTING THE CONTAMINATION OF INDUSTRIAL LIQUIDS

REFERENCE TO RELATED APPLICATION

A method for testing contaminated industrial liquids contained in an enclosed system a vessel, which consists in making the organisms in the liquid release oxygen, is described in copending application, Ser. No. 074,633, filed on Sept. 12, 1979, and assigned to the same assignee. The apparatus of this invention is disclosed but not claimed in said patent application.

BACKGROUND OF THE INVENTION (a) Field of the Invention

This invention relates to an apparatus for testing the contamination of industrial liquids and more particularly for testing the density of mixed or unmixed organisms in such liquids.

(b) Description of the Prior Art

The presence of organisms in an industrial liquid, for example in a metal working fluid, causes rapid deterioration of the fluid and, in the field of cutting oils or lubricants, can cause machine failure. Also, pathogens harmful to man can grow readily in metal working liquids, even when numerous chemical agents are added to kill such organisms. Many of the chemical products used to control such organisms represent serious toxicity hazards and can affect the usefulness of the metal working liquids. To achieve a balanced chemical control requires a very rapid and quantitative testing of the organism density in the liquid.

An important object of this invention is to provide an apparatus for quantitatively assaying organism density in a liquid over a relatively short and known time interval, say in two to twelve minutes, in a liquid sample with no pretreatment of the sample.

In one embodiment the vessel is closed with a stopper. It is desired to measure pressure increases in the vessel's headspace contained above the surface of the liquid. With the apparatus of this invention, the pressure measurements can be made continuously or at different times without loosing the sealing effectiveness of the stopper and, hence, the required measurement accuracy. In another embodiment, it is desired to detect a fixed pressure rise in the gas contained in the vessel.

SUMMARY OF THE INVENTION

One embodiment of the detector measures the pressure rise in a gas contained in a vessel's headspace having gas sealed off from the ambient by a stopper made of an elastic, compressible material. The detector's housing has a bore and at least one port which is in fluid communication with the gas in the vessel. A pressure transducer is disposed in the bore and is in fluid communication with the port. A needle probe is removably coupled to the detector's housing and is in fluid communication with the port. The hollow needle is adapted to pierce the stopper, whereby the pressure transducer becomes responsive to the pressure variations of the gas in the vessel. These pressure variations cause the transducer to generate corresponding electirc signals. The detector's housing preferably has another port open to the ambient pressure, thereby causing the transducer to measure gauge pressure. When the hollow needle is pulled out from the stopper, the vessel again becomes resealed by the stopper.

Another embodiment of the detector includes a threshold, pressure-responsive, electric switch provided with a pair of contacts having one operative condition. The switch has an inlet port for receiving gas pressure from the vessel. An electric circuit couples the contacts of the switch to an indicating device. When the pressure of the gas reaches or exceeds a predetermined threshold pressure, the contacts will switch to another operative condition. The indicating device detects the change in the condition of the contacts in the switch.

BRIEF DESCRIPTION OF THE DRAWINGS

FIG. 1 is a sectional view in elevation of one embodiment of the pressure detector;

FIG. 2 is a sectional view on line 2—2 of FIG. 1;

FIG. 3 is a view in elevation, partly in section, of the pressure detector mounted over a vessel having a volume of liquid and a volume of gas;

FIG. 4 is a schematic block diagram of the transducer used in the detector shown in FIG. 1, together with the associated electric networks for processing the pressures detected by the detector into useful signals.

DETAILED DESCRIPTION OF PREFERRED EMBODIMENTS

Figure 5:
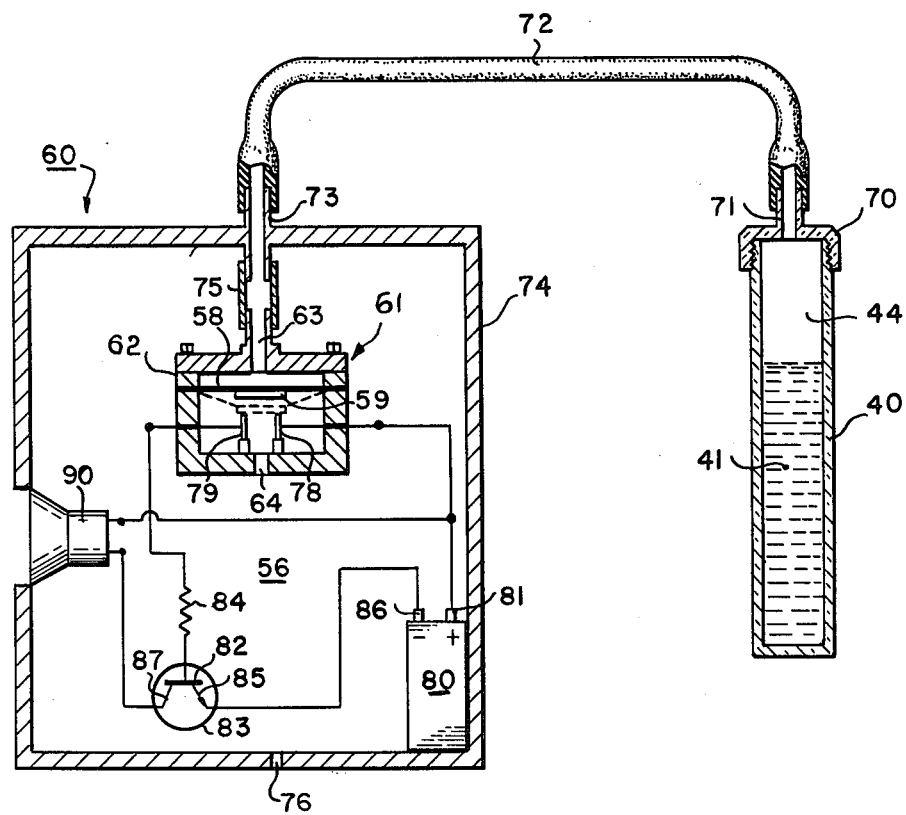
FIG. 5 is a schematic showing of another embodiment of the pressure detector which includes a threshold, pressure-responsive switch used for obtaining an indication when the gas pressure in the vessel exceeds a fixed threshold value.

One embodiment of the detector assembly of this invention is generally designated as 10 (FIGS. 1-3). It includes a housing 12 preferably having a cylindrical configuration as shown. Housing 12 has a bottom face 13 and a top face 14. A large-diameter, axial chamber 15 extends a distance into housing 12 and defines an annular shoulder 16. Chamber 15 is in communication with a small-diameter, coaxial bore 17 which extends to a center port 18 in a cylindrical projection 28.

Mounted in chamber 15 is a pressure transducer, generally designated as 20. Transducer 20 has a pressure-receiving port in a bottom wall 21 and a pressure-receiving port 22a (FIG. 2) in a top wall 22. Transducer 20 converts the difference in pressure applied to its walls 21, 22 into an electric signal transmitted by a cable 24 having an end plug 25. Preferably, the differential pressure transducer 20 is fully embedded in chamber 15 as at 15a, except for an ambient pressure passageway 26 which is in fluid communication with port 22a. The passageway 26 assures reference pressure contact on the active side wall 22 of transducer 20. The port in the bottom wall 21 is in fluid communication with port 18 through a tube 27 which is press fitted into bore 17. Tube 27 provides a passageway 31.

A suitable differential pressure transducer 20 can be purchased from the Foxboro Corporation of San Jose, California, such as Series 1800 which is adapted to measure the absolute pressure or the gauge pressure. This pressure transducer senses pressure by means of a silicon diaphragm into which a fully-active Wheatstone bridge 20a (FIG. 4) has been diffused. The piezo-resistive properties of silicon are utilized to produce a linear output electric signal proportional to the applied pressure or differential pressure. The high signal levels of silicon strain gauges can then be easily amplified, or further conditioned as necessary, to fit the application requirements.

In the preferred embodiment, a leur-lok fitting 30 is epoxied onto projection 28 which downwardly-extends from bottom face 13. Fitting 30 has a central pressure passageway 31a and a screw thread 34 which is adapted to threadedly receive a hollow needle probe housing 36 in a gas-tight manner against a seal 34a. The needle housing 36 permits a wide variety of needles 35 to be attached quickly with a twist into the fitting 30.

The needle probe 36 can detect the pressure in a vessel, generally designated as 40 (FIG. 3), containing a mixture 41 of a contaminated liquid and a reagent. The inlet 42 into the vessel is properly sealed with a stopper 43 made of an elastic, compressible material. Below stopper 43 is a headspace 44. Oxygen becomes generated by the mixture 41, thereby increasing the pressure in the headspace 44.

In use, tip 35' of the hollow needle 35 is shaped to pierce stopper 43 which forms an effective seal around the needle. After the needle 35 pierces through the stopper 43 and enters the headspace 44, the transducer's end wall 21 becomes responsive to the pressure increase in headspace 44. This pressure increase becomes transmitted to end wall 21 through needle 35, needle housing 36, and passageways 31a and 31. After needle 35 is removed from stopper 43, the headspace 44 becomes automatically resealed by the stopper.

An elongated protector sleeve 56 is threadedly coupled to housing 12 to constantly protect needle 35. Protector sleeve 56 assists in maintaining thermal equilibrium by requiring the operator to manipulate vessel 40 near its bottom while vessel 40 is inserted into the detector assembly 10. In this manner, heat transmitted from the operator to the vessel by such handling is at the optimum location of the tube. Thus, tube 56 prevents undesired termal increases from elevating the temperature and concurrently the pressure in headspace 44. Such pressure increases would produce errors in the measurements of the gas produced by the desired organism density.

Cable 24 (FIG. 4) contains a pair of wires 24a feeding current from a current source 50 to the input terminals of the Wheatstone bridge 20a. The output of the bridge is connected to a pair of wires 24b also within cable 24. The pressure rise applied to transducer 20 becomes linearly converted into a corresponding voltage signal at the output of wires 24b which are coupled to a differential amplifier 51. The analog signal from amplifier 51 is digitized by a signal processor 52 and then is recorded and/or displayed by a recording device 53.

If the detector assembly 10 was not measuring the differential pressure between walls 21, 22, that is gauge pressure, variations in the ambient pressure might create corresponding variations in the detected electric signals, thereby introducing substantial erros and precluding the transducer 20 from faithfully reproducing the pressure increases in headspace 44.

In FIG. 5 is shown a modified pressure detector 60 for measuring the pressure increase in vessel 40. Instead of a continuously responsive pressure transducer 20 (FIG. 1), there is now employed a threshold pressure switch, generally designated as 61, mounted in a housing 62 having a passive port 63 and an ambient port 64.

Vessel 40 is sealed with a suitable cap 70 provided with a tubular projection 71 adapted to snugly fit into one end of a flexible tubular member 72. The other end of tubular member 72 snugly fits over a coupling tube 73 in the transducer's housing 74. The internal end of tube 73 is connected to the passive port 63 through a tube 75.

Switch 61 has a pair of contacts 78, 79 which can be closed by a flexible membrane 58 carrying a conductor member 59 in a circuit 56. Contact 78 of the pressure switch 61 is connected to the positive terminal 81 of a battery 80, and terminal 79 is connected to the base 82 of a transistor 83 through a current limiting resistor 84. The emitter 85 of transistor 83 is connected to the negative terminal 86 of the battery. The collector 87 is connected to one terminal of a suitable indicator or alarm 90 whose other terminal is connected to the positive terminal 81 of battery 80. The housing 74 has a port 76 through which ambient pressure is coupled to port 64. Thus, switch 61 will respond to gauge pressure.

In use, when the measured gas pressure in headspace 44 exceeds a fixed pressure threshold, switch 61 will close contacts 78, 79 (dotted position of conductor 59) and circuit 56 will activate the alarm 90. When the pressure is less than the threshold pressure, there will be no alarm action.

Thus, the threshold pressure detector 60 will enable the user to determine whether or not the density of organisms in the liquid 41 exceeds a specified density level.

The embodiment of FIG. 1 is especially adapted for testing cutting fluids, while the embodiment shown in FIG. 5 is especially adapted for testing swimming pool water. Other uses will readily suggest themselves to those skilled in this art.

What is claimed is:

1. A pressure measuring apparatus adapted to periodically measure the pressure in the headspace of a container which is partially filled with a liquid medium containing organisms, the pressure in said headspace depending on the density of said organisms, and said container having an inlet through which said liquid medium is filled into or removed from said container, said apparatus comprising in combination:
    an elastic, compressible stopper for sealing said headspace in said container after said container is filled with said liquid medium to allow said organisms to generate oxygen which increases the gas pressure in said headspace;
    a pressure probe, including a housing having a chamber and a bore defining a passageway, a pressure transducer mounted in said chamber, a hollow piercing element removably coupled to said housing, the interior of said element being in fluid communication with said transducer in said chamber through said passageway, said element having a pointed end portion adapted to pierce through said stopper into said headspace when said housing is pressed against said container, thereby communicating the gas pressure in said headspace to said transducer through the hollow interior of said element and said passageway, the elastic, compressible material of said stopper sealing off said headspace from the ambient before and while said element pierces said stopper, and after said element is withdrawn from said stopper.

2. A method of periodically measuring the pressure in the headspace of a container with a pressure probe, including a housing having a chamber and a bore defining a pasageway, a pressure transducer mounted in said chamber, a hollow piercing element removably coupled to said housing, the interior of said element being in fluid communication with said transducer in said chamber through said passageway, said element having a pointed end, partially filled with a liquid medium containing organisms, the pressure in said headspace depending on the density of said organisms, and said container having an inlet through which said liquid medium is filled into or removed from said container, said method comprising:
- (a) sealing said headspace with an elastic, compressible stopper to allow said organisms to generate oxygen which increases the gas pressure in said headspace,
- (b) pressing said housing against said container to pierce with said element said stopper, thereby communicating the gas pressure in said headspace to said transducer through the hollow interior of said element and said passageway, said elastic, compressible material of said stopper sealing off said headspace from the ambient before and while said element pierces said stopper, and after said element is withdrawn from said stopper.

3. A method for periodically testing the gas pressure in a container having an inlet by using a stopper made from an elastic, compressible material, and a pressure probe having a transducer and a hollow piercing element, comprising:
- (a) partially filling said container with a liquid medium containing organisms,
- (b) plugging up the inlet of said container with said stopper,
- (c) piercing said stopper with said element whereby the hollow interior of said element establishes fluid communication between the headspace in said container and said transducer, thereby obtaining a first measurement of the pressure in said headspace,
- (d) removing said element from said stopper,
  said stopper sealing said headspace from the ambient before and while said element pierces said stopper, and after said element is withdrawn from said stopper, and
- (e) repeating step c) to obtain a second measurement of the pressure in said headspace.

* * * * *